(12) United States Patent
Meng

(10) Patent No.: US 11,352,362 B2
(45) Date of Patent: Jun. 7, 2022

(54) POLYMORPH OF RUCAPARIB CAMSYLATE

(71) Applicant: SHANGHAI BEGREAT PHARMATECH, Shanghai (CN)

(72) Inventor: Xiaoming Meng, Tianjin (CN)

(73) Assignee: SHANGHAI BEGREAT PHARMATECH, Shanghai (CN)

( * ) Notice: Subject to any disclaimer, the term of this patent is extended or adjusted under 35 U.S.C. 154(b) by 107 days.

(21) Appl. No.: 16/854,935

(22) Filed: Apr. 22, 2020

(65) Prior Publication Data

US 2020/0291036 A1    Sep. 17, 2020

Related U.S. Application Data

(63) Continuation of application No. PCT/CN2018/119486, filed on Dec. 6, 2018.

(51) Int. Cl.
*A61K 31/55* (2006.01)
*C07D 223/14* (2006.01)
*C07D 487/04* (2006.01)

(52) U.S. Cl.
CPC ........ *C07D 487/04* (2013.01); *C07B 2200/13* (2013.01)

(58) Field of Classification Search
CPC .............................. A61K 31/55; C07D 223/14

USPC .......................................... 514/217; 540/586
See application file for complete search history.

(56) References Cited

U.S. PATENT DOCUMENTS

2014/0243318 A1    8/2014  Basford et al.
2018/0200260 A1    7/2018  Etter

FOREIGN PATENT DOCUMENTS

CN        108201534 A       6/2018
CN        109111454 A       1/2019
WO        2011098971 A1     8/2011
WO        WO-2018140377 A1 *  8/2018  ........... C07D 487/06

OTHER PUBLICATIONS

International Search Report in PCT/CN2018/119486 dated Jun. 1, 2019, 9 pages.

* cited by examiner

*Primary Examiner* — Douglas M Willis
(74) *Attorney, Agent, or Firm* — Metis IP LLC

(57) ABSTRACT

The present disclosure may disclose a new crystal form D of 8-fluoro-2-{4-[(methylamino)methyl]phenyl}-1,3,4,5-tetrahydro-6H-azepino[5,4,3-cd]indol-6-one ((1S,4R)-7,7-dimethyl-2-oxobicyclo[2.2.1]hept-1-yl) methanesulfonic acid salt, preparation method therefor and a medicinal use. Compared to the existing crystalline forms, this new crystalline form has clear advantages with respect to solubility, stability, and the preparation process.

9 Claims, 6 Drawing Sheets

POLYMORPH OF RUCAPARIB CAMSYLATE

CROSS REFERENCE TO RELATED APPLICATIONS

This application is a continuation of International Patent Application No. PCT/CN2018/119486 filed on Dec. 6, 2018, which is hereby incorporated by reference in its entirety.

TECHNICAL FIELD

The present invention relates to novel crystals of 8-fluoro-2-{4-[(methylamino)methyl]phenyl}-1,3,4,5-tetrahydro-6H-azepino[5,4,3-cd]indol-6-one ((1S,4R)-7,7-dimethyl-2-oxobicyclo[2.2.1]hept-1-yl) methanesulfonic acid salt form D and its preparation method and use.

BACKGROUND

Ovarian cancer is a cancer that originates in a woman's ovaries and produces abnormal cells that invade and metastasize to other areas. The initial symptoms of ovarian cancer are not obvious, and with the progress of the disease, many typical symptoms of cancer appear, including flatulence, abdominal distension, and pelvic pain. Cancer spreads easily to the peritoneum, lymph nodes, lungs, and liver. In 2012, 239,000 women worldwide suffered from ovarian cancer, killing 152,000 people. It is the seventh most common cancer among cancers and the eighth most common cause of death among women. Ovarian cancer is more prevalent in North America and Europe than in Africa and Asia. Polyadenylate diphosphate ribose polymerase (PARP) inhibitors are important DNA repair enzymes that recognize single-strand breaks in DNA to initiate repair. The target drug can inhibit the activity of PARP, and has the effect of enhancing radiotherapy and DNA damage chemotherapy drugs. In addition, it can also selectively kill tumor cells with DNA repair defects. Rucaparib was originally developed by Pfizer. Clovis Oncology obtained its authorization from Pfizer in 2011 and applied for marketing in the United States. It was approved by the US FDA for listing on Dec. 19, 2016 under the trade name Rubraca®. The drug is the second PARP inhibitor on the market and is approved as a monotherapy for patients with advanced ovarian cancer who have undergone BRCA mutations who have received two or more chemotherapy.

Rucaparib Camsylate is chemically named 8-fluoro-2-{4-[(methylamino)methyl]phenyl}-1,3,4,5-tetrahydro-6H-azepino[5,4,3-cd]indol-6-one ((1S,4R)-7,7-dimethyl-2-oxobicyclo[2.2.1]hept-1-yl) methanesulfonic acid salt with molecular formula of $C_{19}H_{18}FN_3O \cdot C_{10}H_{16}O_4S$ and a molecular weight of 555.66, also represented by the structure as follows:

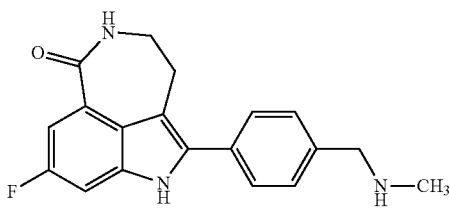

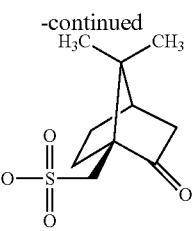

-continued

For chemical raw materials to be formulated, they must have good purity, stability, physical and chemical properties, and operability. These properties are related to the crystal form of the drug. Different crystal forms have different physical and chemical properties. The stability of the drug preservation and the purpose of improving the efficacy of the drug require that the drug be made into a crystal state.

Different crystalline forms of drugs have different solubility and dissolution rates, which affect the bioavailability of drugs, as a result, they can lead to differences in clinical efficacy.

SUMMARY

The main object of the present invention is to provide 8-fluoro-2-{4-[(methylamino)methyl]phenyl}-1,3,4,5-tetrahydro-6H-azepino[5,4,3-cd]indol-6-one ((1S,4R)-7,7-dimethyl-2-oxobicyclo[2.2.1]hept-1-yl) methanesulfonic acid salt (Rucaparib camsylate) new crystalline form D, and process for its preparation and a medicinal use.

A process for the preparation of 8-fluoro-2-{4-[(methylamino)methyl]phenyl}-1,3,4,5-tetrahydro-6H-azepino[5,4,3-cd]indol-6-one ((1S,4R)-7,7-dimethyl-2-oxobicyclo[2.2.1]hept-1-yl) methanesulfonic acid salt crystal form D comprising:
(i) dissolving 8-fluoro-2-{4-[(methylamino)methyl]phenyl}-1,3,4,5-tetrahydro-6H-azepino[5,4,3-cd]indol-6-one ((1S,4R)-7,7-dimethyl-2-oxobicyclo[2.2.1]hept-1-yl) methanesulfonic acid salt in an organic solution;
(ii) the solution obtained in step (i) is placed in an ultrasonic environment, and an antisolvent (a solvent having a low solubility in rucaparib camsylate) is added to precipitate the compound from the solution; and
(iii) obtaining 8-fluoro-2-{4-[(methylamino)methyl]phenyl}-1,3,4,5-tetrahydro-6H-azepino[5,4,3-cd]indol-6-one ((1S,4R)-7,7-dimethyl-2-oxobicyclo[2.2.1]hept-1-yl) methanesulfonic acid salt crystal form D of after liquid-solid separation.

A pharmaceutical composition may comprise t 8-fluoro-2-{4-[(methylamino)methyl]phenyl}-1,3,4,5-tetrahydro-6H-azepino[5,4,3-cd]indol-6-one ((1S,4R)-7,7-dimethyl-2-oxobicyclo[2.2.1]hept-1-yl) methanesulfonic acid salt crystal form D as an active ingredient.

Rucaparib camsylate crystalline form D and its pharmaceutical composition use: for treating cancer.

It is used to treat cancer-related diseases. The disease is selected from breast cancer, ovarian cancer, prostate cancer, and pancreatic cancer, which have the same "PARP gene."

WO2011098971 patent discloses crystalline forms A, B, and C of rucaparib camsylate, but studies have found that crystal forms A, B, and C have low solubility under low pH conditions, such as pH 1.2, which affects the dissolution time of rucaparib camsylate in gastric juice. In practical applications, patients take a relatively high dose of rucaparib camsylate daily. The recommended dose is 600 mg (calculated as rucaparib free base, 300 mg twice daily), and the maximum daily is 1200 mg (calculated as rucaparib free base (600 mg twice daily), or 1030.9 mg and 2061.8 mg if calculated based on rucaparib camsylate. At such high doses, only the compound can be quickly dissolved to ensure that the compound absorbs the drug within the absorption window. For drugs that cannot be dissolved in time, they will not be absorbed by the body which will be wasted and cause unwanted side effects. Compared with the existing crystalline form A, B or C, the crystalline form D of rucaparib camsylate found in the present invention can unexpectedly increase the solubility of rucaparib camsylate in simulated gastric juice, thereby it can make high-dose rucaparib fully absorbed and produce better clinical results with the same dose.

DETAILED DESCRIPTION

The specific embodiments of the present invention are further described in detail below with reference to the drawings and embodiments. The following examples are intended to illustrate the invention, but are not intended to limit the scope of the invention.

The X-ray powder diffraction operation and analysis steps in this patent are as follows:

The Rigaku Ultima IV powder diffractometer was used, which was irradiated with Cu-K(R) (40 kV, 40 mA) at room temperature using a D/tex Ultra detector. The scanning range is from 3° to 45° in the 2θ interval, and the scanning speed is 20°/min.

Measurement differences associated with X-ray powder diffraction analysis results are produced by a variety of factors including: (a) errors in sample preparation (e.g., sample height), (b) instrument error, (c) calibration differences, (d) operator error (including errors that occur when determining peak position), and (e) properties of the substance (e.g., preferred orientation error). Calibration errors and sample height errors often result in displacement of all peaks in the same direction. When using a flat sampler, small differences in sample height will result in large displacements of the XRPD peak position. Systematic studies have shown that a 1 mm sample height difference can result in a 2θ peak shift of up to 1θ. These displacements can be identified from the X-ray diffraction pattern and can be eliminated by compensating for the displacement (using a system calibration factor for all peak position values) or recalibrating the instrument. As described above, the measurement errors from different instruments can be corrected by applying a system calibration factor to make the peak positions consistent.

Example 1

Dissolve 50 mg of rucaparib camsylate in 1 ml of diethyl oxalate, place the solution within bottle in an ultrasonic water bath, and add an anti-solvent acetonitrile under the ultrasonic working environment to produce a precipitate and rucaparib camsylate Form D was obtained.

Figure 1:
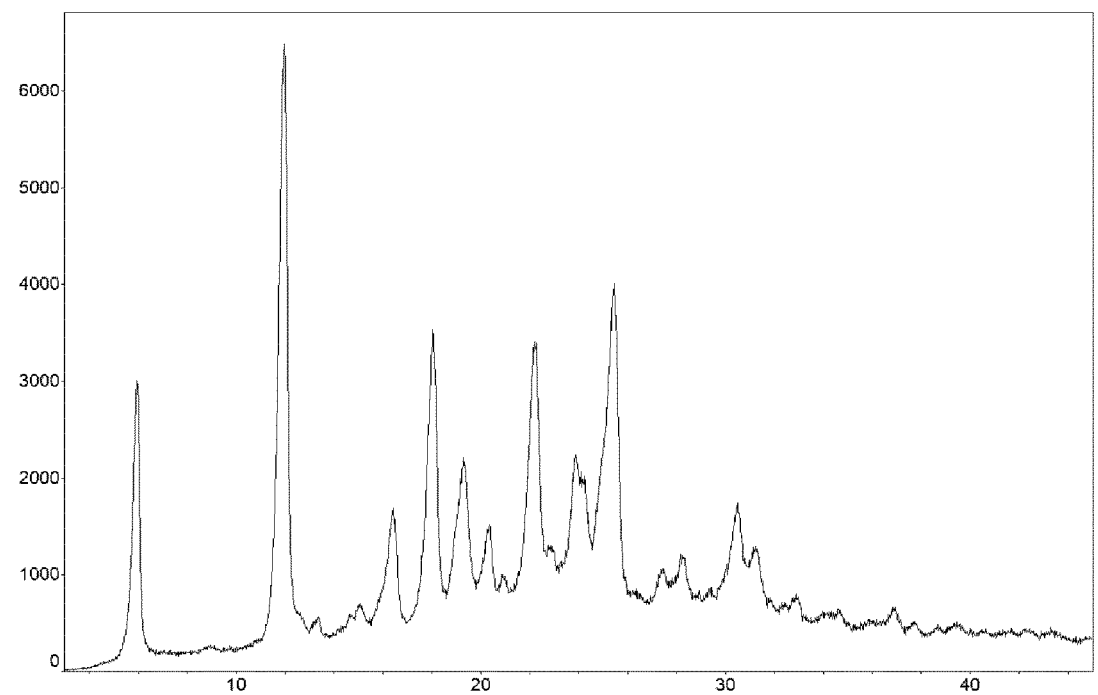
FIG. 1 is an XPRD pattern of rucaparib camsylate form D. 2θ values in unit of degree in accordance with the abscissa. The intensity of diffraction peak as ordinate.

In the present invention, the rucaparib camsylate form D, the XRPD patterns is shown in FIG. 1 and the diffraction peaks of the XRPD pattern of Form III are listed in the following table:

| 2-Theta | d(Å) | I(Height) % |
|---|---|---|
| 6.0 | 14.7651 | 46.6 |
| 12.0 | 7.3568 | 100 |
| 16.5 | 5.3749 | 19.3 |
| 18.1 | 4.9024 | 46.2 |
| 19.3 | 4.5857 | 22.1 |
| 20.4 | 4.3499 | 10.5 |
| 22.3 | 3.9904 | 40.1 |
| 23.9 | 3.714 | 17 |
| 25.5 | 3.4902 | 48.2 |
| 30.5 | 2.9248 | 14.8 |
| 31.3 | 2.8571 | 5 |

Figure 2:
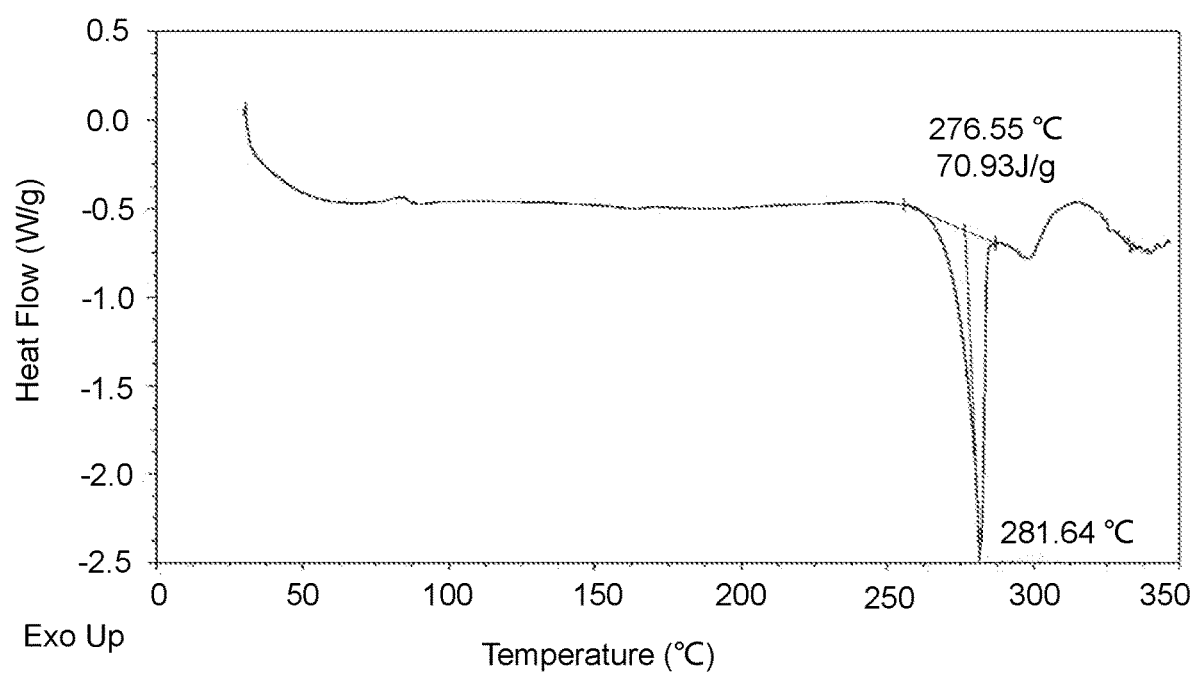
FIG. 2 is a DSC plot of rucaparib camsylate Form D. Temperature in unit of ° C. in accordance with the abscissa. The Heat flow (w/g) as ordinate.
Figure 3:
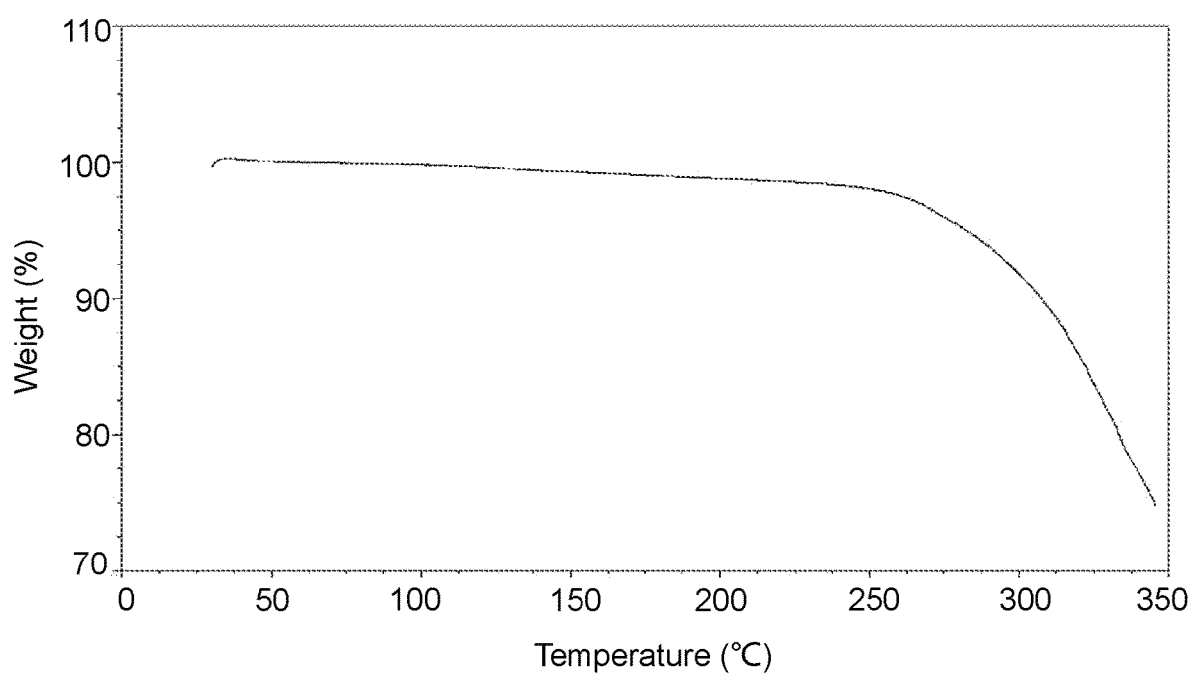
FIG. 3 is a TGA plot of rucaparib camsylate Form D. Temperature in unit of ° C. in accordance with the abscissa. The Weight (%) as ordinate.

A differential scanning calorimetry (DSC) analysis was performed on the crystal Form D in Example 1, using a TA Q2000 differential scanning calorimeter using an $N_2$ atmosphere at a temperature rising rate of 10° C./min. The DSC plot of Form D is shown in FIG. 2. The melting point of Form D is 276.6° C. (onset temperature). The thermogravimetric (TGA) analysis of the crystal Form D in Example 1 was carried out using a TA Q500 thermogravimetric analyzer using a $N_2$ atmosphere at a heating rate of 10° C./min. The TGA plot of Form I is shown in FIG. 3.

Example 2

Dissolve 50 mg of rucaparib camsylate in 1 ml of ethanol, place the solution within bottle in an ultrasonic water bath, and add an anti-solvent acetonitrile under the ultrasonic working environment to produce a precipitate and rucaparib camsylate Form D was obtained. The XRPD pattern of the crystal form D obtained in this example is consistent with FIG. 1.

Example 3

Dissolve 50 mg of rucaparib camsylate in 1 ml of ethanol/diethyl oxalate mixture, place the solution within bottle in an ultrasonic water bath, and add an anti-solvent acetonitrile under the ultrasonic working environment to produce a precipitate and rucaparib camsylate Form D was obtained. The XRPD pattern of the crystal form D obtained in this example is consistent with FIG. 1.

Example 4

Dissolve 50 mg of rucaparib camsylate in 1 ml of diethyl oxalate, place the solution within bottle in an ultrasonic water bath, and add an anti-solvent 2-butanone under the ultrasonic working environment to produce a precipitate and rucaparib camsylate Form D was obtained. The XRPD pattern of the crystal form D obtained in this example is consistent with FIG. 1.

Example 5

In order to evaluate the physical stability of the crystal form D, experiments on the stress stability for the crystal form D were performed. The physical stability of the crystal form D under high temperature, high humidity and light stress conditions was investigated. The experimental conditions of the stress stability are as follows:

| Item | Conditions | | Pull point |
|---|---|---|---|
| Stress stability | Elevate temperature | 60° C. | 5, 10 day |
| | High humidity | 92.5% RH | 5, 10 day |
| | Light stress | 4500 lux | 5, 10 day |

Figure 4:
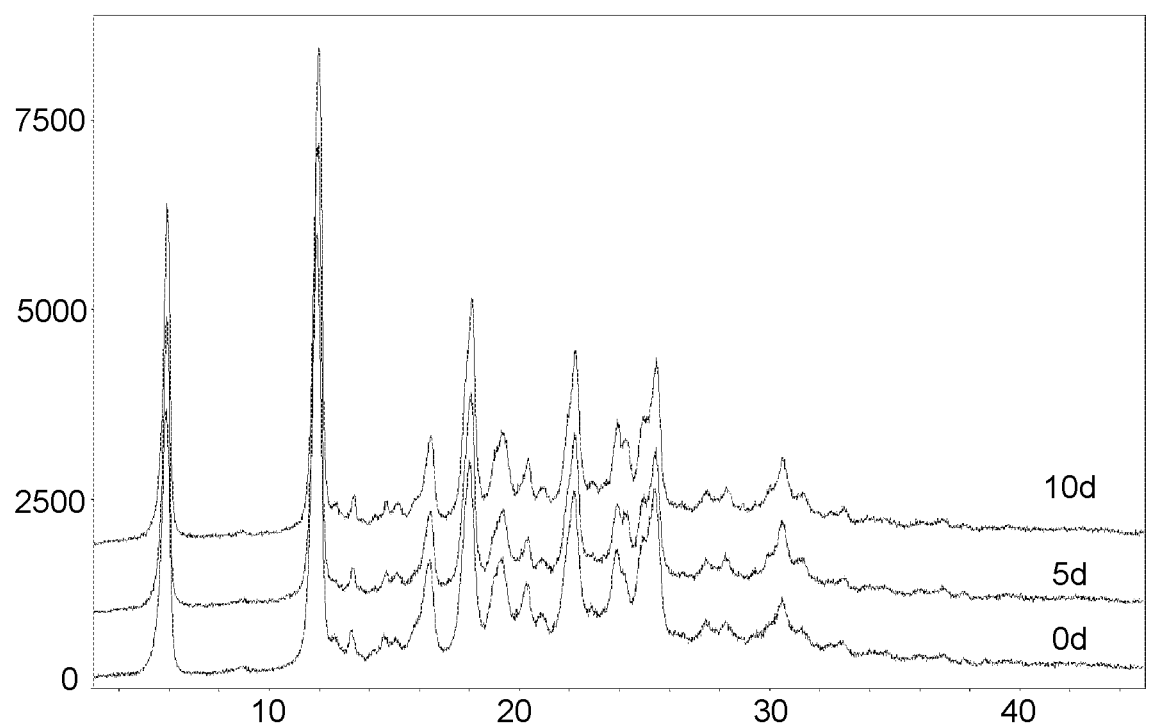
FIG. 4 is an XPRD pattern of rucaparib camsylate form D after forced degradation treatment (elevated temperature). 2θ values in unit of degree in accordance with the abscissa. The intensity of diffraction peak as ordinate.
Figure 5:
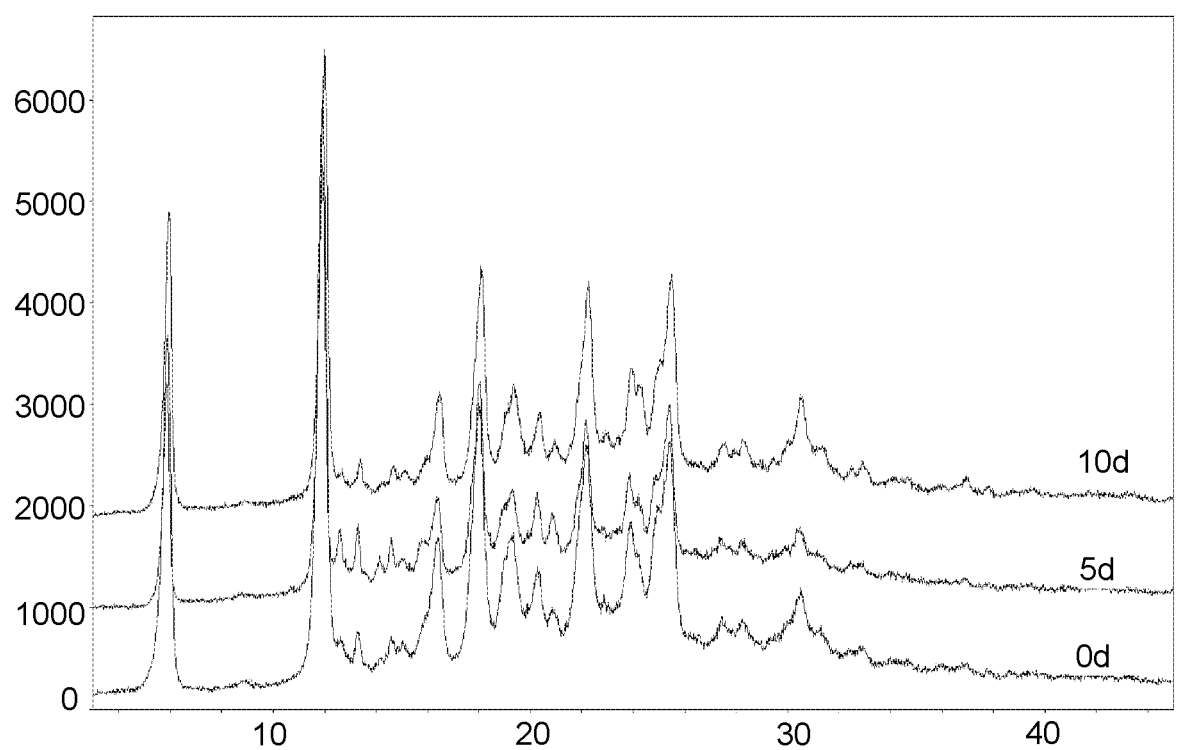
FIG. 5 is an XPRD pattern of rucaparib camsylate form D after forced degradation treatment (high humid). 2θ values in unit of degree in accordance with the abscissa. The intensity of diffraction peak as ordinate.
Figure 6:
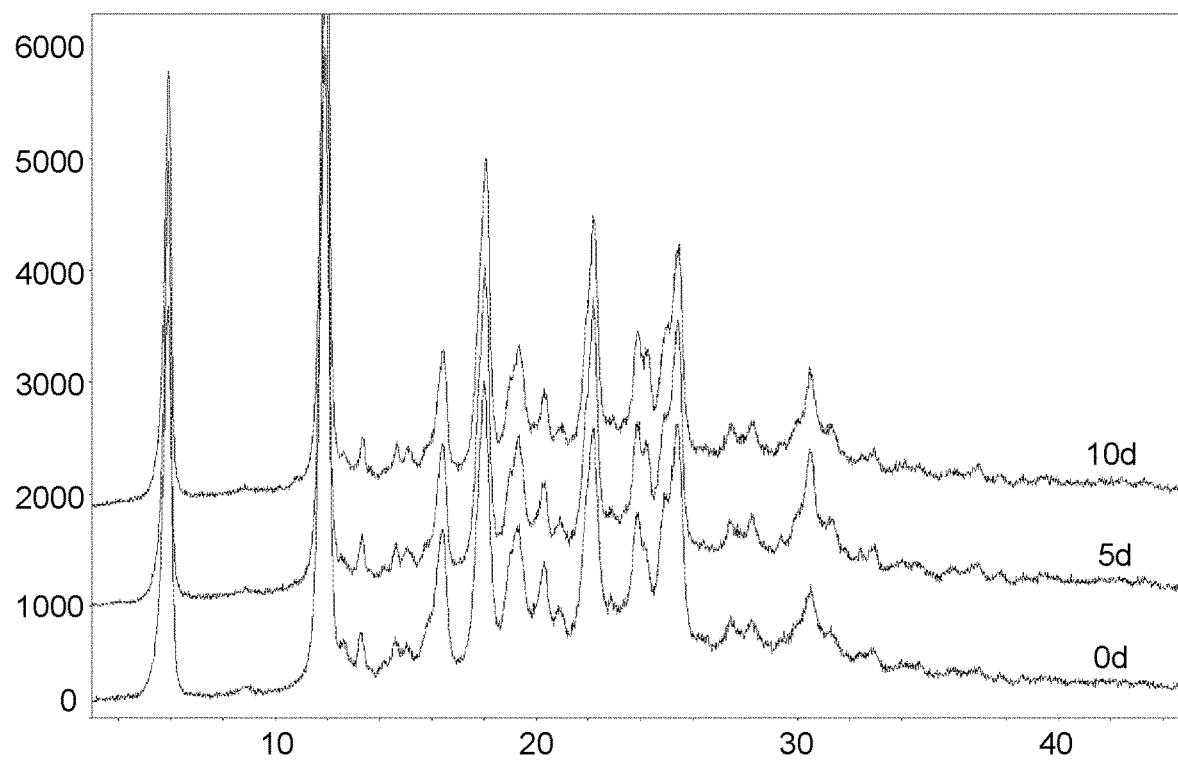
FIG. 6 is an XPRD pattern of rucaparib camsylate form D after forced degradation treatment (light stability). 2θ values in unit of degree in accordance with the abscissa. The intensity of diffraction peak as ordinate.

The crystal form D was placed in the above stress conditions. After sampling at the time point, the stability sample was evaluated by XRPD. The results are summarized as follows:

| Stress condition | | Initial sample | 5 day | 10 day | XRPD pattern |
|---|---|---|---|---|---|
| Elevate temperature | 60° C. | Form D | Form D | Form D | FIG. 4 |
| High humidity | 92.5% RH | Form D | Form D | Form D | FIG. 5 |
| Light stress | 4500 lux | Form D | Form D | Form D | FIG. 6 |

The experimental results of stress stability show that the crystal form D is stable under the conditions of high temperature, high humidity and light stress conditions. This indicates that Form D is a very physically stable form and is suitable for drug development.

Example 6

Determination of the solubility of rucaparib camsylate in simulated gastric juice. Weigh about 1 mg of the powder of Form A, Form B, Form C and Form D of rucaparib camsylate in a 2-mL tube, then add 1 mL of simulated gastric juice (Prepared by adding diluted hydrochloric acid 16.4 ml, 800 ml of water and 10 g of pepsin. After shaking, add water to volume of 1000 ml). After shaking the suspension for 20 min, it was filtered through a needle filter to obtain a clear solution. The rucaparib camsylate content in the solution was analyzed by HPLC method.

| Crystal forms of rucaparib camsylate | Source | Solubility in SGF (mg/mL) |
|---|---|---|
| Form A | Prepared according to | 0.10 |
| Form B | WO2011098971 | 0.13 |
| Form C | | 0.11 |
| Form D | Example 1 | 0.31 |

From the above results, it can be seen that the crystalline form D of rucaparib camsylate can be rapidly dissolved under low pH conditions, and the solubility at 20 minutes is significantly higher than that of the existing crystalline forms A, B and C. The recommended dose of rucaparib is 600 mg (calculated as rucaparib free base, 300 mg twice daily), and the maximum daily is 1200 mg (calculated by rucaparib free base, 600 mg twice daily). If calculated according to rucaparib camsylate salt, the daily take of the salt will be 1030.9 mg and 2061.8 mg. At such high doses, the compound must be dissolved rapidly in large quantities to ensure that the compound absorbed within the absorption window. For drug that cannot be dissolved in time, it will not be absorbed completely by the body. The unabsorbed drug will be wasted and cause unwanted side effects. The solubility and dissolution rate of new rucaparib camsylate Form D in simulated gastric juice is significantly higher than that of the prior art crystalline form, so that high-dose rucaparib can be fully absorbed, and the better clinical effect obtained at the same dose.

What is claimed is:

1. A crystal Form D of 8-fluoro-2-{4-[(methylamino)methyl]phenyl}-1,3,4,5-tetrahydro-6H-azepino[5,4,3-cd]indol-6-one ((1S,4R)-7,7-dimethyl-2-oxobicyclo[2.2.1]hept-1-yl)methanesulfonic acid salt of the formula:

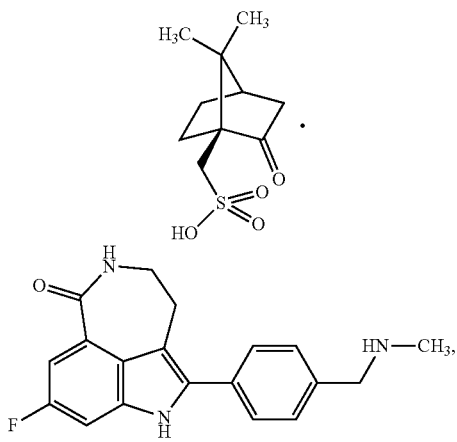

wherein the crystal Form D is characterized by an X-ray powder diffraction pattern comprising characteristic diffraction peaks at angles (°2θ) of 6.0°±0.2 °2θ, 12.0°±0.2 °2θ, and 25.5°±0.2 °2θ; and
wherein the X-ray powder diffraction pattern is determined on a diffractometer using CuKα radiation.

2. The crystal Form D of claim 1, wherein the crystal Form D is further characterized by an X-ray powder diffraction pattern comprising additional characteristic diffraction peaks at angles (°2θ) of 18.1°±0.2 °2θ and 22.3°±0.2 °θ.

3. The crystal Form D of claim 1, wherein the crystal Form D is further characterized by an X-ray powder diffraction pattern comprising additional characteristic diffraction peaks at angles (°2θ) of 16.5°±0.2 2θ, 18.1°±0.2 °2θ, 19.3°±0.2 °2θ, 22.3°±0.2 °2θ, and 23.9°±0.2 °2θ.

4. The crystal Form D of claim 1, wherein the crystal Form D is further characterized by an X-ray powder diffraction pattern comprising additional characteristic diffraction peaks at angles (°2θ) of 16.5°±0.2 °2θ, 18.1°±0.2 °2θ, 19.3°±0.2 °2θ, 20.4°±0.2 °2θ, 22.3°±0.2 °2θ, 23.9°±0.2 °2θ, 30.5°±0.2 °2θ, and 31.3°±0.2°2θ.

5. The crystal Form D of claim 1, wherein the crystal Form D is further characterized by an X-ray powder diffraction pattern as depicted in FIG. 1.

6. A pharmaceutical composition comprising a pharmaceutically acceptable excipient and the crystal Form D of claim 1 as an active ingredient.

7. A method for treating a cancer in a patient in need thereof, wherein the method comprises administering to the patient a therapeutically effective amount of the pharmaceutical composition of claim 6.

8. The method of claim 7, wherein the cancer is selected from the group consisting of breast cancer, ovarian cancer, pancreatic cancer, and prostate cancer.

9. A process for the preparation of the crystal Form D of 8-fluoro-2-{4-[(methylamino)methyl]phenyl}-1,3,4,5-tetrahydro-6H-azepino[5,4,3-cd]indol-6-one ((1S,4R)-7,7-dimethyl-2-oxobicyclo[2.2.1]hept-1-yl)methanesulfonic acid salt according to claim 1 of the formula:

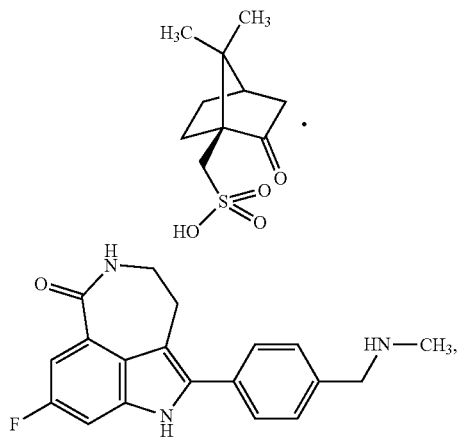

wherein the process comprises the following steps:

(i) dissolving 8-fluoro-2-4-[(methylamino)methyl]phenyl-1,3,4,5-tetrahydro-6H-azepino[5,4,3-cd]indol-6-one ((1S,4R)-7,7-dimethyl-2-oxobicyclo[2.2.1]hept-1-yl)methanesulfonic acid salt in an organic solvent selected from the group consisting of diethyl oxalate and ethanol, or a mixture thereof, to obtain a solution;

(ii) placing the solution obtained in step (i) in an ultrasonic water bath;

(iii) adding an antisolvent selected from the group consisting of acetonitrile and 2-butanone, or a mixture thereof, to the solution obtained in step (i), to afford precipitation of 8-fluoro-2-{4-[(methylamino)methyl]phenyl}-1,3,4,5-tetrahydro-6H-azepino[5,4,3-cd]indol-6-one ((1S,4R)-7,7-dimethyl-2-oxobicyclo[2.2.1]hept-1-yl)methanesulfonic acid salt from the solution; and (iv) obtaining the crystal Form D of 8-fluoro-2-4-[(methylamino)methyl]phenyl-1,3,4,5-tetrahydro-6H-azepino[5,4,3-cd]indol-6-one ((1S,4R)-7,7-dimethyl-2-oxobicyclo[2.2.1]hept-1-yl)methanesulfonic acid salt.

* * * * *